United States Patent
Mou et al.

(10) Patent No.: US 10,881,787 B2
(45) Date of Patent: *Jan. 5, 2021

(54) WEARABLE LIQUID SUPPLYING DEVICE FOR HUMAN INSULIN INJECTION

(71) Applicant: Microjet Technology Co., Ltd., Hsinchu (TW)

(72) Inventors: Hao-Jan Mou, Hsinchu (TW); Li-Pang Mo, Hsinchu (TW); Wei-Ming Lee, Hsinchu (TW); Chi-Feng Huang, Hsinchu (TW); Yung-Lung Han, Hsinchu (TW)

(73) Assignee: MICROJET TECHNOLOGY CO., LTD., Hsinchu (TW)

(*) Notice: Subject to any disclaimer, the term of this patent is extended or adjusted under 35 U.S.C. 154(b) by 204 days.

This patent is subject to a terminal disclaimer.

(21) Appl. No.: 16/149,713

(22) Filed: Oct. 2, 2018

(65) Prior Publication Data
US 2019/0125964 A1 May 2, 2019

(30) Foreign Application Priority Data
Oct. 27, 2017 (TW) .............................. 106137202 A (51) Int. Cl.
*A61M 31/00* (2006.01)
*A61M 5/142* (2006.01)
(Continued)

(52) U.S. Cl.
CPC .... *A61M 5/14248* (2013.01); *A61M 5/14224* (2013.01); *A61M 5/158* (2013.01);
(Continued)

(58) Field of Classification Search
CPC .... A61M 2037/0023; A61M 2039/224; A61M 2039/265; A61M 2205/0294;
(Continued)

(56) References Cited

U.S. PATENT DOCUMENTS 6,132,755 A * 10/2000 Eicher ................ A61M 31/002
424/427
6,623,457 B1 * 9/2003 Rosenberg .......... A61B 17/205
604/191

(Continued)

FOREIGN PATENT DOCUMENTS

CN 106860972 A 6/2017
TW M352999 U 3/2009

OTHER PUBLICATIONS

Extended European Search Report for European Application No. 18198127.5, dated Feb. 12, 2019.

*Primary Examiner* — Rebecca E Eisenberg
(74) *Attorney, Agent, or Firm* — Birch, Stewart, Kolasch & Birch, LLP (57) ABSTRACT

A wearable liquid supplying device for human insulin injection is fixed on a body of human through a ring belt and includes a substrate, a flow-guiding-and-actuating unit, a sensor and a driving chip. The substrate has a liquid storage chamber. The flow-guiding-and-actuating unit has a liquid guiding channel in communication with a liquid storage outlet of the liquid storage chamber and a liquid guiding outlet. The sensor measures a blood glucose level and generates measured data correspondingly. The driving chip receives the measured data from the sensor and controls the actuation of the flow-guiding-and-actuating unit and the open/closed states of the switching valves. The flow-guiding-and-actuating unit is enabled to generate a pressure difference so that the insulin liquid is transported to the liquid guiding outlet through the liquid guiding channel and flows into the microneedle patch for allowing the microneedles to inject the insulin liquid into the subcutaneous tissue.

20 Claims, 10 Drawing Sheets (51) Int. Cl.
*A61M 5/158* (2006.01)
*A61M 5/32* (2006.01)
*F04B 43/04* (2006.01)
*F04B 23/02* (2006.01)
*A61M 5/168* (2006.01)
*A61M 37/00* (2006.01)
*A61M 5/172* (2006.01)
*A61B 5/00* (2006.01)

(52) U.S. Cl.
CPC ...... *A61M 5/16813* (2013.01); *A61M 5/3295* (2013.01); *A61M 37/0015* (2013.01); *F04B 23/02* (2013.01); *F04B 43/043* (2013.01); *F04B 43/046* (2013.01); *A61B 5/4266* (2013.01); *A61M 2005/1726* (2013.01); *A61M 2037/003* (2013.01); *A61M 2037/0023* (2013.01); *A61M 2205/0244* (2013.01); *A61M 2205/0288* (2013.01); *A61M 2205/0294* (2013.01); *A61M 2205/8206* (2013.01); *A61M 2209/088* (2013.01); *A61M 2210/083* (2013.01); *A61M 2230/201* (2013.01)

(58) Field of Classification Search
CPC .. A61M 2205/3303; A61M 2205/8206; A61M 2230/201; A61M 37/0015; A61M 39/26; A61M 5/14224; A61M 5/14248; A61M 5/14593; A61M 5/16813; A61M 5/16881; A61M 5/1723
See application file for complete search history.

(56) References Cited

U.S. PATENT DOCUMENTS

| | | | |
|---|---|---|---|
| 2011/0142688 A1* | 6/2011 | Chappel | F04B 43/043 417/213 |
| 2012/0095400 A1 | 4/2012 | Hanson et al. | |
| 2012/0172833 A1 | 7/2012 | Zisapel | |
| 2012/0277667 A1 | 11/2012 | Yodat et al. | |
| 2015/0057611 A1* | 2/2015 | Bureau | A61M 37/0015 604/111 |
| 2016/0045158 A1 | 2/2016 | Hsu | |
| 2017/0014572 A1 | 1/2017 | Newberry et al. | |
| 2017/0095184 A1* | 4/2017 | Heikenfeld | A61B 5/0531 |
| 2019/0143090 A1* | 5/2019 | Baker | A61M 37/0015 604/506 |
| 2019/0223795 A1* | 7/2019 | Patolsky | A61B 5/14532 |

* cited by examiner

WEARABLE LIQUID SUPPLYING DEVICE FOR HUMAN INSULIN INJECTION

FIELD OF THE INVENTION

The present disclosure relates to a liquid supplying device, and more particularly to a wearable liquid supplying device for human insulin injection.

BACKGROUND OF THE INVENTION

Nowadays, the way of curing people with type 1 Diabetes mellitus or type 2 Diabetes mellitus is to supply hypoglycemic medicines for the people. Methods of delivering medicines to patients include oral, syringe injection and insulin pump injection. Regarding the methods of oral and syringe injection, the patient needs to take a drop of blood, measure the blood glucose level by using a blood glucose meter and take medicines according to the measured data every day. Regarding the method of insulin pump injection, an insulin pump system includes an indwelling needle and an insulin pump. The indwelling needle punctures into the patient's skin and fixed on the patient's body for lancing a drop of blood and injecting medicines. The insulin pump is in fluid communication with the indwelling needle and is controlled to release hypoglycemic medicines according to the measured blood glucose level.

Insulin cannot be directly taken by mouth but can be administered through injection. However, the syringe or the indwelling needle of the insulin pump are required when the injection method is performed. The syringe and the indwelling needle not only cause patient pain but also leave pinhole on the patient's skin. Especially, syringe injection needs to be performed plural times a day. Under this circumstance, the subcutaneous tissue may generate hard block due to frequent injections. Although the insulin pump may reduce the number of injections by using the indwelling needle, it is inconvenient to carry the insulin pump and dispose the indwelling needle on the patient's body in daily life or to go out for sport due to relatively huge volume and heavy weight.

Therefore, there is a need of providing a wearable liquid supplying device for human insulin injection to address the above-mentioned issues as using the conventional injection method. The wearable liquid supplying device for human insulin injection is intelligent, safe, portable and painless and allows the patient to inject human insulin in daily life so as to control the blood glucose level anytime.

SUMMARY OF THE INVENTION

The object of the present disclosure is to provide a wearable liquid supplying device for human insulin injection to overcome the current situation, wherein the conventional insulin injection method causes the patient pain and it is inconvenient to carry the insulin pump. The wearable liquid supplying device for human insulin injection is intelligent, safe, portable and painless and allows the patient to inject human insulin in daily life so as to control the blood glucose level anytime. The wearable liquid supplying device for human insulin injection is served as an artificial pancreas for supplying human insulin automatically.

In accordance with an aspect of the present disclosure, a wearable liquid supplying device for human insulin injection is provided. The wearable liquid supplying device includes a main body, a ring belt, a substrate, a liquid storage chamber, a flow-guiding-and-actuating unit, plural switching valves, a microneedle patch, a sensor and a driving chip. The main body has an accommodation space. The ring belt has two ends connected to two sides of the main body. The substrate is disposed in the accommodation space of the main body. The liquid storage chamber is disposed on the substrate for storing insulin liquid and has a liquid storage outlet. The flow-guiding-and-actuating unit is disposed on the substrate and has a liquid guiding channel in fluid communication with the liquid storage outlet of the liquid storage chamber and has a liquid guiding outlet in fluid communication with the liquid guiding channel, wherein the flow-guiding-and-actuating unit is enabled to transport the insulin liquid to be discharged out through the liquid guiding outlet. The switching valves have a first switching valve disposed in the liquid storage outlet and a second switching valve disposed in the liquid guiding outlet. The microneedle patch is disposed under the flow-guiding-and-actuating unit to seal the liquid guiding outlet and has plural microneedles with hollow structures to be punctured into skin of human body via microinvasive technology so that the insulin liquid is injected into subcutaneous tissue. The sensor is disposed on the substrate and configured to be in contact with the skin of the human body for measuring a blood glucose level in sweat and generating measured data correspondingly. The driving chip is disposed on the substrate and configured to control the actuation of the flow-guiding-and-actuating unit, control open/closed states of the plural switching valves, receive the measured data from the sensor and determine an action according to the measured data from the sensor. When the ring belt is worn on the skin of the human body, the plural microneedles of the microneedle patch are punctured into the skin of the human body. When the sensor measures the blood glucose level in the sweat from the skin of the human body and generate specific measured data correspondingly, the driving chip controls the actuation of the flow-guiding-and-actuation unit, controls the first switching valve in the liquid storage outlet to be in open state and controls the second switching valve in the liquid guiding outlet to be in open state so that the insulin liquid within the liquid storage chamber is discharged through the liquid guiding outlet and flows into the microneedle patch, by which the insulin liquid is further discharged through the plural microneedles with the hollow structures and injected into the subcutaneous tissue.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Figure 1:
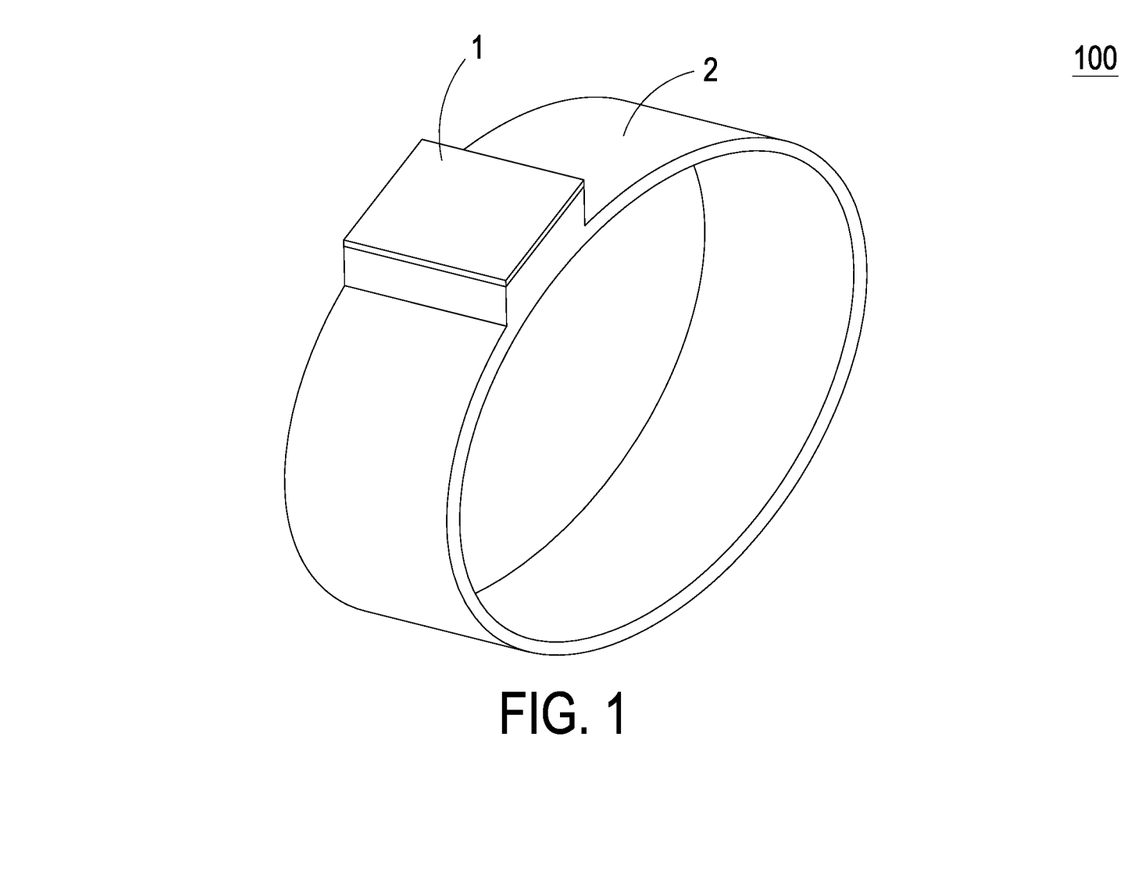
FIG. 1 is a schematic structural view illustrating a wearable liquid supplying device for human insulin injection according to an embodiment of the present disclosure.
Figure 2:
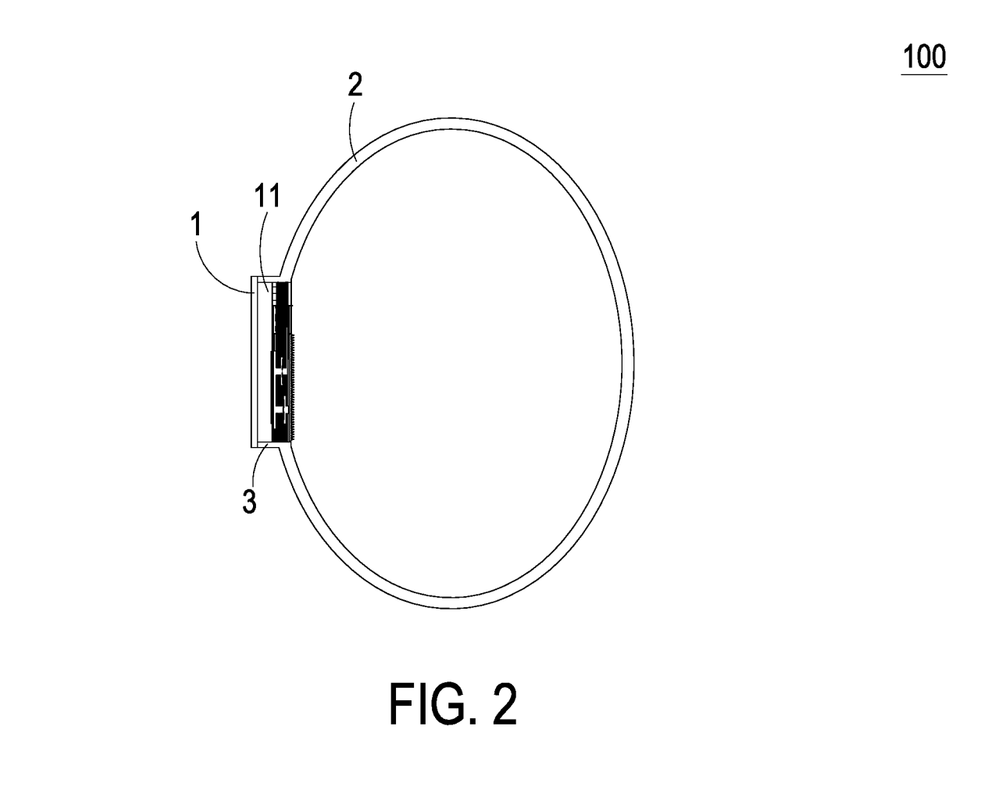
FIG. 2 is a cross sectional view illustrating the wearable liquid supplying device for human insulin injection of FIG. 1.
Figure 3:
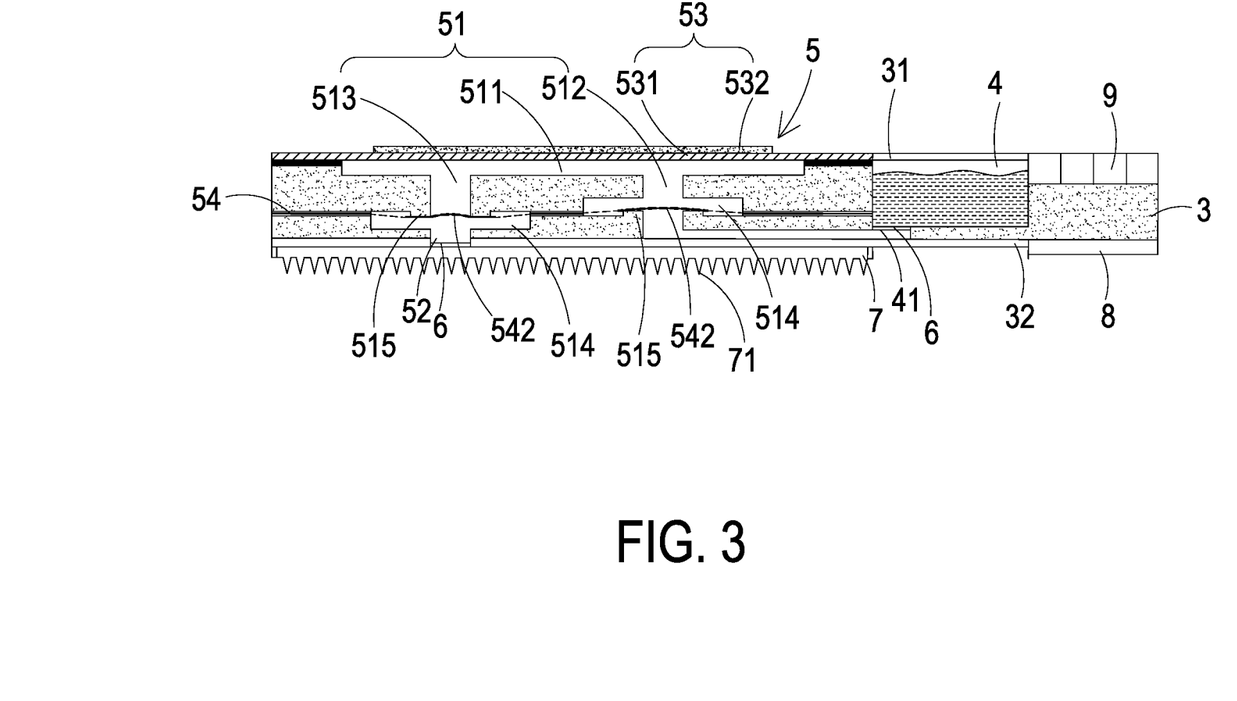
FIG. 3 is a cross sectional view illustrating portions of the wearable liquid supplying device for human insulin injection of FIG. 2.

Please refer to FIGS. 1 to 3. The present discourse provides a wearable liquid supplying device 100 for human insulin injection including at least one main body 1, at least one accommodation space 11, at least one ring belt 2, at least one substrate 3, at least one liquid storage chamber 4, at least one liquid storage outlet 41, at least one flow-guiding-and-actuating unit 5, at least one liquid guiding channel 51, at least one liquid guiding outlet 52, at least one switching valve 6, at least one microneedle patch 7, at least one sensor 8, at least one driving chip 9 and at least one specific measured data of a blood glucose level. The number of the main body 1, the accommodation space 11, the ring belt 2, the substrate 3, the liquid storage chamber 4, the liquid storage outlet 41, the flow-guiding-and-actuating unit 5, the liquid guiding channel 51, the liquid guiding outlet 52, the switching valve 6, the microneedle patch 7, the sensor 8, the driving chip 9 and the specific measured data of the blood glucose level is exemplified by one for each in the following embodiments but not limited thereto. It is noted that each of the main body 1, the accommodation space 11, the ring belt 2, the substrate 3, the liquid storage chamber 4, the liquid storage outlet 41, the flow-guiding-and-actuating unit 5, the liquid guiding channel 51, the liquid guiding outlet 52, the switching valve 6, the microneedle patch 7, the sensor 8, the driving chip 9 and the specific measured data of the blood glucose level can also be provided in plural numbers.

Figure 8:
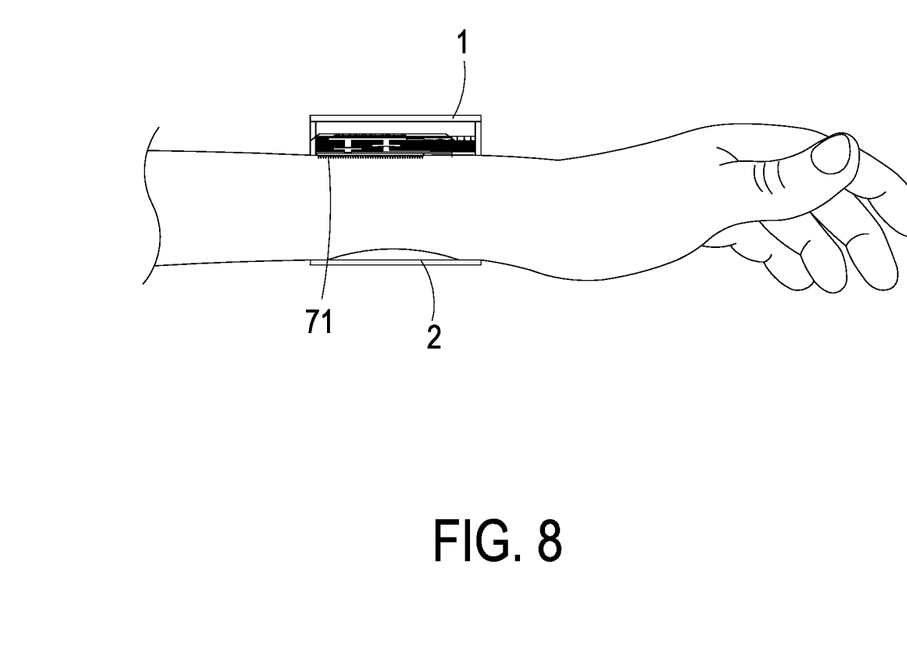
FIG. 8 is a schematic structural view illustrating the wearable liquid supplying device for human insulin injection to be worn on user's body.

The present disclosure discloses a wearable liquid supplying device 100 for human insulin injection. Please refer to FIGS. 1, 2 and 3. The wearable liquid supplying device 100 for human insulin injection includes a main body 1, a ring belt 2, a substrate 3, a liquid storage chamber 4, a flow-guiding-and-actuating unit 5, plural switching valves 6, a microneedle patch 7, a sensor 8 and a driving chip 9. The main body 1 has an accommodation space 11. The ring belt 2 has two ends connected to two sides of the main body 1 so that the main body 1 may be fixed on user's body through the ring belt 2 (see FIG. 8). For example, the main body 1 may be fixed on a wrist, an ankle or a neck of the user for wearable purpose that enhances the portability to carry it around. The substrate 3 is accommodated within the accommodation space 11 of the maim body 1. The liquid storage chamber 4 is concavely formed on the substrate 3 to store the human insulin liquid and has a liquid storage outlet 41 for discharging the insulin liquid within the liquid storage chamber 4. The liquid storage chamber 4 concavely formed on the substrate 3 is sealed with a cover 31. The flow-guiding-and-actuating unit 5 is disposed on the substrate 3 and has a flow guiding channel 51 and a liquid guiding outlet 52. The flow-guiding channel 51 is in fluid communication with the liquid storage outlet 41 of the liquid storage chamber 4. The flow-guiding-and-actuating unit 5 is enabled to generate a suction force so that the insulin liquid within the liquid storage chamber 4 is drawn out through the liquid storage outlet 41 in fluid communication with the flow-guiding channel 51, flows into the flow-guiding-and-actuating unit 5 and is discharged through the liquid guiding outlet 52. In this embodiment, the number of the plural switching valves 6 is two, but not limited thereto. The switching valves 6 are disposed in the liquid storage outlet 41 and the liquid guiding outlet 52 to seal the liquid storage outlet 41 and the liquid guiding outlet 52, respectively. The switching valves 6 are controlled to be in an open state or in a closed state so that the amount of the insulin liquid to be transported through the liquid storage outlet 41 and the liquid guiding outlet 52 is controlled, by which the conditions of supplying excessive or insufficient insulin can be prevented. The microneedle patch 7 is attached on a bottom of the flow-guiding-and-actuating unit 5 and thus covers the liquid guiding outlet 52. The microneedle patch 7 has plural microneedles 71 with hollow structures. After the microneedles 71 with the hollow structures are punctured into the skin of the human body via noninvasive or microinvasive technologies, the insulin liquid may be discharged through the liquid guiding outlet 52 and then injected into the subcutaneous tissue. The sensor 8 and the driving chip 9 are integrated on the substrate 1 by using a microelectron-mechanical systems (MEMS) procedure. The sensor 8 is disposed on the substrate 3 and in contact with the skin of the user's body for measuring the blood glucose level in sweat, by which the measured data of the blood glucose level can be acquired. In addition, the main body 1 has a through hole (not shown) adjacent to the skin of the user's body. The through hole is in communication with the accommodation space 11 and allows the microneedle patch 7 to install therethrough so as to contact with the user's skin.

The microneedles 71 of the microneedle patch 7 are micron-sized needles capable of puncturing the patient's skin. The microneedles 71 may be made of a material such as a high molecular polymer, a metal or silicon. Preferably but not exclusively, the microneedles 71 are made of silicon dioxide with high biocompatibility. The microneedles 71 have specific diameters for allowing the insulin molecules to pass through. Preferably, the microneedle 71 has an internal diameter ranging from 10 μm to 550 μm. The microneedle 71 has a length ranging from 400 μm to 900 μm. The microneedles 71 can puncture into the subcutaneous tissue of the human body till a depth without contacting any nerve so that the user is painless. The microneedles 71 are disposed on the microneedle patch 7 and arranged in an array. The microneedles 71 are spaced from each other a distance greater than 200 μm so that the injection flow from the microneedles 71 may not interfere with each other. Under circumstances when blockage of one or more microneedles 71 occurs, the microneedles 71 arranged in the array can prevent the flow injection function from being impacted and allow the rest of the microneedles 71 to maintain the flow injection function continuously.

Please refer to FIG. 3. The liquid guiding channel 51 of the flow-guiding-and-actuating unit 5 includes a compressing chamber 511, an inlet channel 512 and an outlet channel 513. The inlet channel 512 is in fluid communication with liquid storage outlet 41 of the liquid storage chamber 4. The outlet channel 513 is in fluid communication with the liquid guiding outlet 52. The inlet channel 512 and the outlet channel 513 run through the substrate 3 and are separated from each other. The compressing chamber 511 is concavely formed on the substrate 3 and is in fluid communication with one end of the inlet channel 512 and one end of the outlet channel 513. An actuator 53 covers and seals the compressing chamber 511. The inlet channel 512 is disposed on the substrate 3 and the other end of the inlet channel 512 is covered by a covering component 32 so that the other end of the inlet channel 512 is in fluid communication with the liquid storage outlet 41 of the liquid storage chamber 4 to form a sealed fluid channel. The other end of the outlet channel 513 has an outlet aperture to be severed as the liquid guiding outlet 52. Consequently, the inlet channel 512, the compressing chamber 511, the outlet channel 513 and the liquid guiding outlet 52 are connected in series and are in fluid communication with each other to form a fluid path.

The flow-guiding-and-actuating unit 5 further includes the actuator 53. The actuator 53 includes a carrying member 531 and an actuating element 532. The carrying member 531 covers and seals the compressing chamber 511, and the actuating element 532 is attached on the surface of the carrying member 531. The actuating element 532 may be subject to deformation that drives the carrying member 531 to vibrate up and down. In this way, the volume of the compressing chamber 511 is changeable that influences the pressure inside the compressing chamber 511 so as to generate a suction force to transport the insulin liquid.

Please refer to FIGS. 3 and 5 again. A valve membrane 54 is disposed in both of the inlet channel 512 and the outlet channel 513 of the flow-guiding-and-actuating unit 5. The substrate 3 includes a chamber 514 and a convex structure 515 located at a middle part of the inlet channel 512, and includes a chamber 514 and a convex structure 515 located at a middle part of the outlet channel 513. In the middle part of the inlet channel 512, the convex structure 515 is disposed on the bottom of the chamber 514. In the middle part of the outlet channel 513, the convex structure 515 is disposed on the top of the chamber 514. In any one of the corresponding chambers 514, the valve membrane 54 has plural through holes 541 and has a central part 542 connected to plural connection parts 543 so that the central part 542 can be elastically supported by the connection parts 543. Consequently, the valve membrane 54 covers the chambers 514 located at the inlet channel 512 and the outlet channel 513, where each convex structure 515 provide a pre-force that abuts against the central part 542.

Figure 4A:
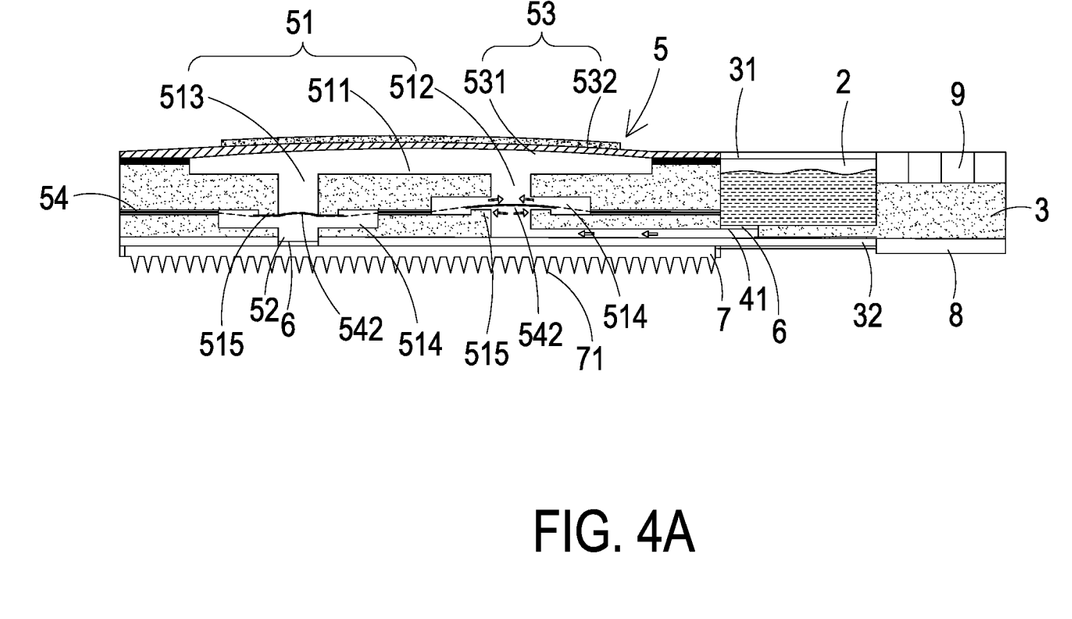
FIGS. 4A and 4B show the actuations of the wearable liquid supplying device for human insulin injection of FIG. 3.
Figure 4B:
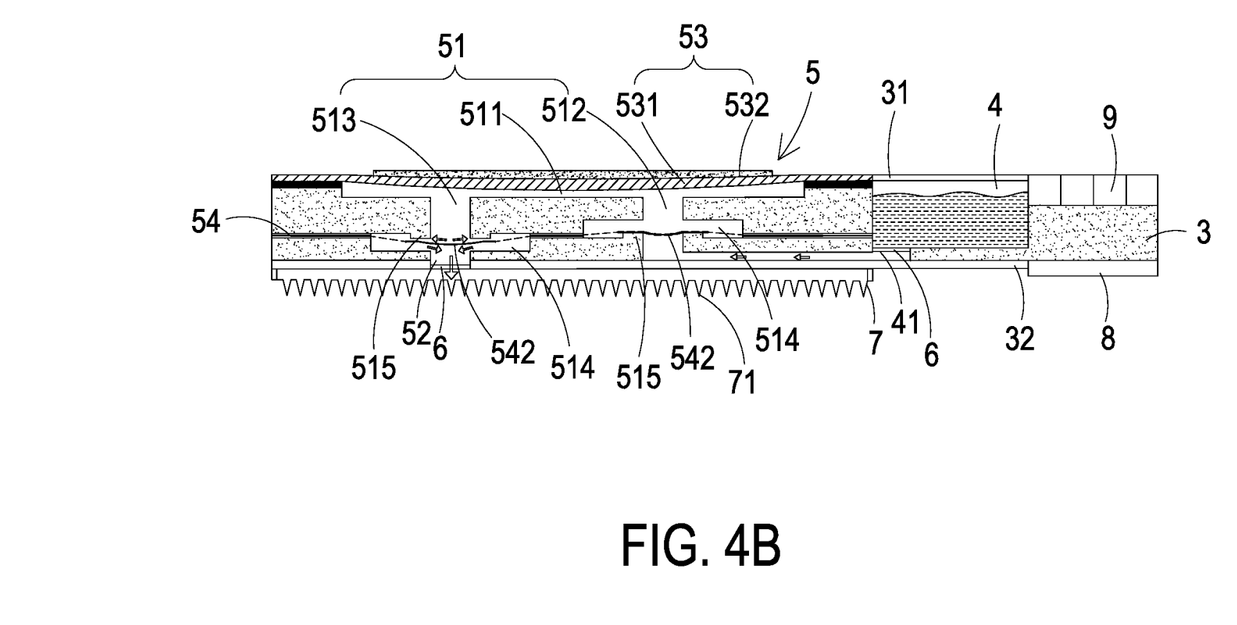
Figure 5:
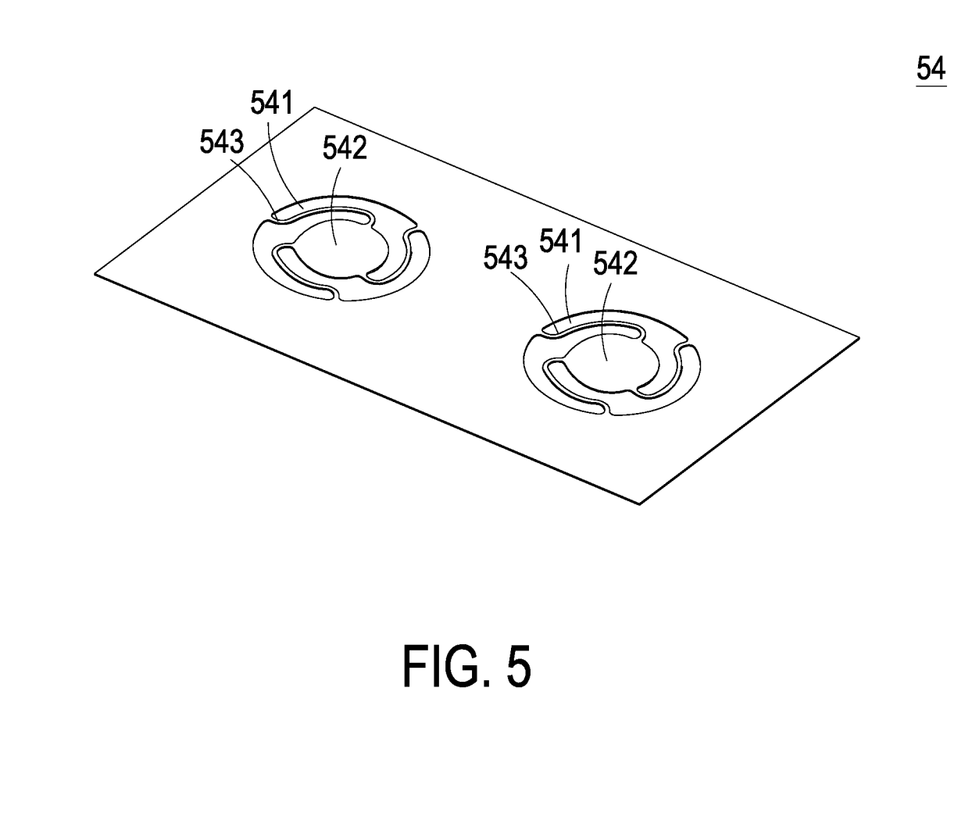
FIG. 5 is a schematic structural view illustrating the valve membrane of the wearable liquid supplying device for human insulin injection according to the present disclosure.

As shown in FIGS. 4A, 4B and 5, when the switching valve 6 in the liquid storage outlet 41 is in the open state, the flow-guiding-and-actuating unit 5 is enabled to generate a pressure difference therein so as to drive the central part 542 of the valve membrane 54 in the inlet channel 512 to move upwardly and away from the convex structure 515 in the inlet channel 512. Consequently, the insulin liquid in the inlet channel 512 can flow into the compressing chamber 511 through the at least one through hole 541 of the valve membrane 54. Referring to FIG. 4B, after the insulin liquid flows into the compressing chamber 511, in response to the pressure difference within the flow-guiding-and-actuating unit 5, the central part 542 of the valve membrane 54 in the outlet channel 513 moves downwardly and away from the convex structure 515 in the outlet channel 513 so that the insulin liquid flows toward the liquid guiding outlet 52. By utilizing the structures described above, when the actuator 53 is non-enabled, the central parts 542 of the valve membrane 54 in the inlet channel 512 and the outlet channel 513 can seal the inlet channel 512 and the outlet channel 513, respectively. This design allows the insulin liquid to be transported between the inlet channel 512 and the outlet channel 513 without flowing back.

Figure 6A:
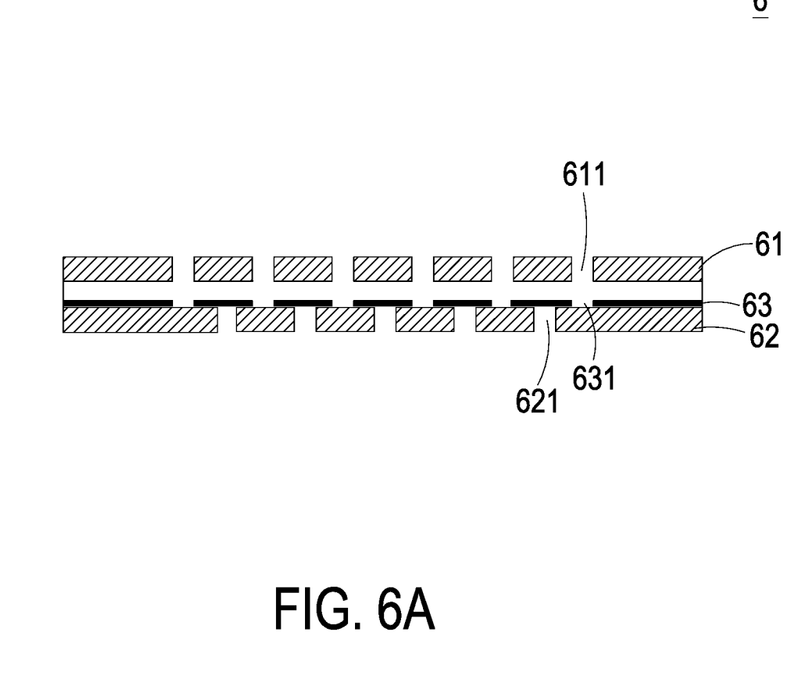
FIG. 6A is a schematic structural view illustrating the switching valve of the wearable liquid supplying device for human insulin injection according to the present disclosure.
Figure 6B:
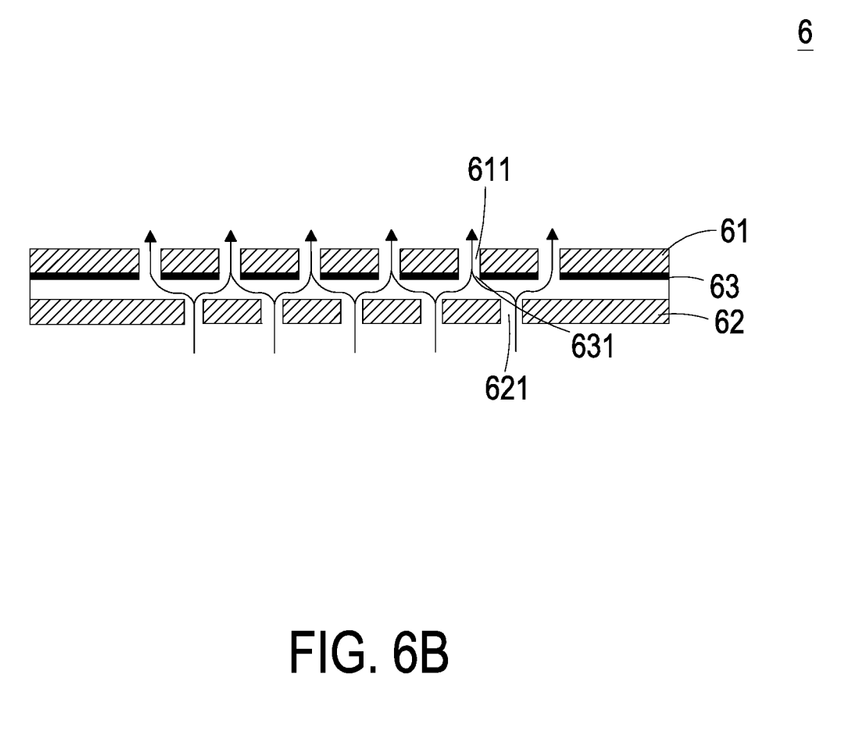
FIG. 6B is schematic diagram illustrating the actuation of switching valve of FIG. 6A.

As shown in FIGS. 6A and 6B, the switching valve 6 includes a stationary component 61, a sealing component 62 and a displacement component 63. The displacement component 63 is disposed and moves between the stationary component 61 and the sealing component 62. The stationary component 61 has at least two first orifices 611. The displacement component 63 has at least two second orifices 631 respectively corresponding in position to the at least two first orifices 611 of the stationary component 61. That is, the at least two first orifices 611 of the stationary component 61 are aligned with the at least two second orifices 631 of the displacement component 63. The sealing component 62 has at least one third orifice 621. The at least one third orifice 621 of the sealing component 62 is misaligned with the at least two first orifices 611 of the stationary component 61 and the at least two second orifices 631 of the displacement component 63. In an embodiment, the stationary component 61, the sealing component 62 and the displacement component 63 are made of a graphene material so as to form a miniature valve element.

In a first aspect of the switching valve 6 in the present disclosure, the displacement component 63 is made of a charged material, and the stationary component 61 is made of a bipolar conductive material. The stationary component 61 is electrically connected to a control circuit of the driving chip 9, so that the change electrical polarity (positive polarity or negative polarity) of the stationary component 61 can be controlled by the driving chip 9. In case that the displacement component 63 is made of a negative charged material, while the switching valve 6 is required to be opened, the stationary component 61 is in positive polarity in response to the control of the driving chip 9. Since the displacement component 63 and the stationary component 61 are maintained in opposite polarity, the displacement component 63 moves toward the stationary component 61 to open the switching valve 6 (as shown in FIG. 6B). In contrast, in case that the displacement component 63 is made of the negative charged material, while the switching valve 6 is required to be closed, the stationary component 61 is in negative polarity in response to the control of the driving chip 9. Since the displacement component 63 and the stationary component 61 are maintained in the same polarity, the displacement component 63 moves toward the sealing component 62 to close the switching valve 6 (as shown in FIG. 6A).

In a second aspect of the switching valve 6 in the present disclosure, the displacement component 63 is made of a magnetic material, and the stationary component 61 is made of an electromagnet material and can be controlled to change its magnetic polarity. The stationary component 61 is electrically connected to the control circuit of the driving chip 9. The driving chip 9 is used to change the magnetic polarity (positive polarity or negative polarity) of the stationary component 61. In case that the displacement component 63 is made of a magnetic material and has negative polarity, while the switching valve 6 is required to be opened, the stationary component 61 is in positive polarity in response to the control of the driving chip 9. Since the displacement component 63 and the stationary component 61 are maintained in opposite polarity under control of the driving chip 9, the displacement component 63 moves toward the stationary component 61 to open the switching valve 6 (as shown in FIG. 6B). In contrast, in case that the displacement component 63 is made of a magnetic material and has negative polarity, while the switching valve 6 is required to be closed, the stationary component 61 is in negative polarity in response to the control of the driving chip 9. Since the displacement component 63 and the stationary component 61 are maintained in the same polarity, the displacement component 63 moves toward the sealing component 62 to close the switching valve 6 (as shown in FIG. 6A).

Figure 7:
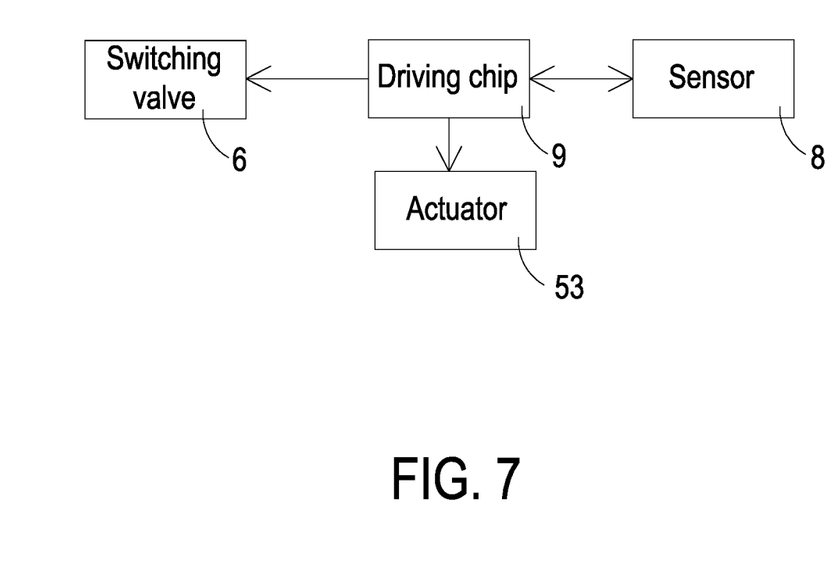
FIG. 7 is a circuit block diagram of the wearable liquid supplying device for human insulin injection according to the embodiment of the present disclosure.

Please refer to FIG. 7, which is a circuit block diagram of the wearable liquid supplying device for human insulin injection according to the embodiment of the present disclosure. The driving chip 9 is disposed on the substrate 3 and electrically connected to the flow-guiding-and-actuating unit 5, plural switching valves 6 and the sensor 8. The sensor 8 is in contact with the skin of the human body to measure the blood glucose level in sweat and generate a corresponding measured data of the blood glucose level. The driving chip 9 receives the measured data from the sensor 8 and determines whether to enable the flow-guiding-and-actuating unit 5 and open the switching valves 6 to perform an operation regarding the insulin liquid injection. Preferably but not exclusively, the driving chip 9 includes a graphene battery (not shown) to supply power.

In summary, the present disclosure provides a wearable liquid supplying device for human insulin injection. The flow-guiding-and-actuating unit is enabled to generate a pressure difference so as to transport the insulin liquid within the liquid storage chamber. Then, the insulin liquid is injected into the user's skin through microneedle patch so as to supply the insulin for the user. The sensor measures the blood glucose level of the user, and the driving chip controls the actuation of the flow-guiding-and-actuating unit and the open and closed states of the switching valves so as to adjust the amount and flow rate of the insulin liquid to be injected into the user. Thus, the wearable liquid supplying device for human insulin injection of the present disclosure can provide the functions of pancreas and be served as a substitution of an artificial pancreas.

While the disclosure has been described in terms of what is presently considered to be the most practical and preferred embodiments, it is to be understood that the disclosure needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A wearable liquid supplying device for human insulin injection, comprising:
   a main body having an accommodation space;
   a ring belt having two ends connected to two sides of the main body;
   a substrate disposed in the accommodation space of the main body;
   a liquid storage chamber disposed on the substrate for storing insulin liquid and having a liquid storage outlet;
   a flow-guiding-and-actuating unit disposed on the substrate, wherein the flow-guiding-and-actuating unit has a liquid guiding channel in fluid communication with the liquid storage outlet of the liquid storage chamber and has a liquid guiding outlet in fluid communication with the liquid guiding channel, wherein the flow-guiding-and-actuating unit is enabled to transport the insulin liquid and then discharge the insulin liquid through the liquid guiding outlet;
   plural switching valves having a first switching valve disposed in the liquid storage outlet and a second switching valve disposed in the liquid guiding outlet;
   a microneedle patch disposed under the flow-guiding-and-actuating unit to seal the liquid guiding outlet and having plural microneedles with hollow structures for puncturing into skin of human body via microinvasive technology so as to inject the insulin liquid into subcutaneous tissue of the human body;
   a sensor disposed on the substrate and configured to be in contact with the skin of the human body for measuring a blood glucose level in sweat and generating measured data correspondingly; and
   a driving chip disposed on the substrate and configured to control the actuation of the flow-guiding-and-actuating unit, control open/closed states of the plural switching valves, receive the measured data from the sensor and determine an action according to the measured data from the sensor;
   wherein when the ring belt is worn on the skin of the human body, the plural microneedles of the microneedle patch are punctured into the skin of the human body, wherein when the sensor measures the blood glucose level in the sweat from the skin of the human body and generates a specific measured data correspondingly, the driving chip controls the actuation of the flow-guiding-and-actuation unit, controls the first switching valve in the liquid storage outlet to be in open state and controls the second switching valve in the liquid guiding outlet to be in open state so that the insulin liquid within the liquid storage chamber is discharged through the liquid guiding outlet and flows into the microneedle patch, whereby the insulin liquid is further discharged through the plural microneedles with the hollow structures and injected into the subcutaneous tissue.

2. The wearable liquid supplying device for human insulin injection according to claim 1, wherein the flow guiding channel of the flow-guiding-and-actuation unit comprises a compressing chamber, an inlet channel and an outlet channel, wherein the inlet channel is in fluid communication with the liquid storage outlet of the liquid storage chamber, the outlet channel is in fluid communication with the liquid guiding outlet, and the inlet channel and the outlet channel are separated from each other and are in fluid communication with each other through the compressing chamber, and wherein the flow-guiding-and-actuating unit has an actuator sealing the compressing chamber, and the actuator is capable of compressing the volume of the compressing chamber for allowing and pushing the insulin liquid to flow.

3. The wearable liquid supplying device for human insulin injection according to claim 2, wherein the flow-guiding-and-actuating unit comprises a carrying member and an actuating element, wherein the carrying member covers the compressing chamber, and the actuating element is attached to a surface of the carrying member, wherein the actuating element is subject to deformation that drives the carrying member to vibrate up and down so as to compress the volume of the compressing chamber for allowing and pushing the insulin liquid to flow.

4. The wearable liquid supplying device for human insulin injection according to claim 3, wherein the actuating element is a piezoelectric component.

5. The wearable liquid supplying device for human insulin injection according to claim 2, wherein a valve membrane is disposed in the inlet channel and the outlet channel for controlling the inlet channel and the outlet channel to be in an open state or a closed state while the flow-guiding-and-actuating unit is enabled to change the volume of the compressing chamber.

6. The wearable liquid supplying device for human insulin injection according to claim 5, wherein the substrate has convex structures in the inlet channel and the outlet channel, wherein each convex structure provides a pre-force that abuts against the valve membrane, thereby preventing the insulin liquid from flowing back.

7. The wearable liquid supplying device for human insulin injection according to claim 1, wherein the driving chip comprises a graphene battery for providing power.

8. The wearable liquid supplying device for human insulin injection according to claim 1, wherein the switching valve comprises a stationary component, a sealing component and a displacement component, wherein the displacement component is disposed between the stationary component and the sealing component, the stationary component has plural first orifices, the displacement component has plural second orifices, and the sealing component has plural third orifices, wherein the plural first orifices of the stationary component are aligned with the plural second orifices of the displacement component, and the plural third orifices of the sealing component are misaligned with the plural first orifices of the stationary component and the plural second orifices of the displacement component.

9. The wearable liquid supplying device for human insulin injection according to claim 8, wherein the displacement component is made of a charged material, and the stationary component is made of a bipolar conductive material, wherein the displacement component and the stationary component are maintained in opposite polarity, and the displacement component moves toward the stationary component so that the switching valve is in the open state.

10. The wearable liquid supplying device for human insulin injection according to claim 9, wherein the polarity of the stationary component is controlled by the driving chip.

11. The wearable liquid supplying device for human insulin injection according to claim 8, wherein the displacement component is made of a charged material, and the stationary component is made of a bipolar conductive material, wherein the displacement component and the stationary component are maintained in the same polarity, and the displacement component moves toward the sealing component so that the switching valve is in the closed state.

12. The wearable liquid supplying device for human insulin injection according to claim 11, wherein the polarity of the stationary component is controlled by the driving chip.

13. The wearable liquid supplying device for human insulin injection according to claim 8, wherein the displacement component is made of a magnetic material, and the stationary component is made of an electromagnet material whose magnetic polarity is changeable under control, wherein the displacement component and the stationary component are maintained in opposite polarity, and the displacement component moves toward the stationary component so that the switching valve is in the open state.

14. The wearable liquid supplying device for human insulin injection according to claim 13, wherein the polarity of the stationary component is controlled by the driving chip.

15. The wearable liquid supplying device for human insulin injection according to claim 8, wherein the displacement component is made of a magnetic material, and the stationary component is made of an electromagnet material whose magnetic polarity is changeable under control, wherein the displacement component and the stationary component are maintained in the same polarity, and the displacement component moves toward the sealing component so that the switching valve is in the closed state.

16. The wearable liquid supplying device for human insulin injection according to claim 15, wherein the polarity of the stationary component is controlled by the driving chip.

17. The wearable liquid supplying device for human insulin injection according to claim 1, wherein each of the plural microneedles of the microneedle patch has an internal diameter ranging from 10 µm to 550 µm and has a length ranging from 400 µm to 900 µm.

18. The wearable liquid supplying device for human insulin injection according to claim 1, wherein the plural microneedles with the hollow structures are arranged in an array, and the plural microneedles with the hollow structures are spaced from each other a distance greater than 200 µm.

19. The wearable liquid supplying device for human insulin injection according to claim 1, wherein the plural microneedles with the hollow structures are made of silicon dioxide.

20. A wearable liquid supplying device for human insulin injection, comprising:
   at least one main body having at least one accommodation space;
   at least one ring belt having two ends connected to two sides of the main body;
   at least one substrate disposed in the accommodation space of the main body;
   at least one liquid storage chamber disposed on the substrate for storing insulin liquid and having at least one liquid storage outlet;
   at least one flow-guiding-and-actuating unit disposed on the substrate, wherein the flow-guiding-and-actuating unit has at least one liquid guiding channel in fluid communication with the liquid storage outlet of the liquid storage chamber and has at least one liquid guiding outlet in fluid communication with the liquid guiding channel, wherein the flow-guiding-and-actuating unit is enabled to transport the insulin liquid and then discharge the insulin liquid through the liquid guiding outlet;
   plural switching valves having at least one first switching valve disposed in the liquid storage outlet and at least one second switching valve disposed in the liquid guiding outlet;
   at least one microneedle patch disposed under the flow-guiding-and-actuating unit to seal the liquid guiding outlet and having plural microneedles with hollow structures for puncturing into skin of human body via microinvasive technology so as to inject the insulin liquid into subcutaneous tissue of the human body;
   at least one sensor disposed on the substrate and configured to be in contact with the skin of the human body for measuring a blood glucose level in sweat and generating measured data correspondingly; and
   at least one driving chip disposed on the substrate and configured to control the actuation of the flow-guiding-and-actuating unit, control open/closed states of the plural switching valves, receive the measured data from the sensor and determine an action according to the measured data from the sensor;
   wherein when the ring belt is worn on the skin of the human body, the plural microneedles of the microneedle patch are punctured into the skin of the human body, wherein when the sensor measures the blood glucose level in the sweat from the skin of the human body and generates at least one specific measured data correspondingly, the driving chip controls the actuation of the flow-guiding-and-actuation unit, controls the first switching valve in the liquid storage outlet to be in open state and controls the second switching valve in the liquid guiding outlet to be in open state so that the insulin liquid within the liquid storage chamber is discharged through the liquid guiding outlet and flows into the microneedle patch, whereby the insulin liquid is further discharged through the plural microneedles with the hollow structures and injected into the subcutaneous tissue.

* * * * *